(12) United States Patent
Vogel et al.

(10) Patent No.: US 8,901,484 B2
(45) Date of Patent: Dec. 2, 2014

(54) QUANTIFICATION OF IMPURITIES FOR RELEASE TESTING OF PEPTIDE PRODUCTS

(71) Applicant: Sanofi-Aventis Deutschland GmbH, Frankfurt am Main (DE)

(72) Inventors: Martin Vogel, Frankfurt am Main (DE); Werner Mueller, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/870,288

(22) Filed: Apr. 25, 2013

(65) Prior Publication Data

US 2013/0284912 A1 Oct. 31, 2013

Related U.S. Application Data

(60) Provisional application No. 61/665,098, filed on Jun. 27, 2012.

(30) Foreign Application Priority Data

Apr. 27, 2012 (EP) .................. PCT/EP2012/057771

(51) Int. Cl.
*H01J 49/26* (2006.01)
*G01N 33/68* (2006.01)
*H01J 49/00* (2006.01)

(52) U.S. Cl.
CPC ............ *H01J 49/26* (2013.01); *G01N 33/6848* (2013.01); *G01N 2333/605* (2013.01); *H01J 49/00* (2013.01)

USPC ........ 250/281; 250/282; 210/198.2; 210/635; 210/656; 435/4; 435/6.1; 514/5.9; 530/303; 530/308; 73/61.52

(58) Field of Classification Search
USPC ............... 250/281–300; 210/198.2, 635, 656; 435/4, 6.1; 514/5.9; 530/303, 308; 73/61.52
See application file for complete search history.

(56) References Cited

U.S. PATENT DOCUMENTS

| | | | |
|---|---|---|---|
| 7,871,519 B2 * | 1/2011 | Kurata et al. | 210/635 |
| 2009/0180953 A1 * | 7/2009 | Gotthardt et al. | 424/1.69 |
| 2011/0137022 A1 * | 6/2011 | Michaud et al. | 536/25.34 |
| 2011/0213131 A1 * | 9/2011 | Christensen et al. | 530/399 |
| 2012/0295846 A1 * | 11/2012 | Hagendorf et al. | 514/6.5 |

FOREIGN PATENT DOCUMENTS

WO WO 2012/012352 A2 1/2012

OTHER PUBLICATIONS

Leib et al., "Direct Quantitation of Peptide Mixtures without Standards Using Clusters Formed by Electrospray Ionization Mass Spectrometry", Analytical Chemistry (2009), vol. 81, No. 10, pp. 3965-3972.

(Continued)

*Primary Examiner* — Michael Logie

(57) ABSTRACT

The present invention relates to a method for the quantitative determination of an impurity present in a peptide product, wherein the impurity cannot be separated from other impurities or the main product. The method particularly involves the use of high resolution mass spectrometry (MS) detection with or without high performance liquid chromatography (HPLC). The method can be used for the investigation of the quality of peptides and proteins, particularly of pharmaceutical peptides and proteins.

4 Claims, 11 Drawing Sheets

(56) References Cited

OTHER PUBLICATIONS

Gygi et al., "Quantitative analysis of complex protein mixtures using isotope-coded affinity tags", Nature Biotechnology (1999), vol. 17, No. 10, pp. 994-999.

Xie et al., "Characterization of Protein Impurities and Site-Specific Modifications Using Peptide Mapping with Liquid Chromatography and Data Independent Acquisition Mass Spectrometry", Analytical Chemistry (2009), vol. 81, No. 14, pp. 5699-5708.

International Search Report dated Feb. 7, 2013 issued in PCT/EP2012/057771.

Laursen, et al., "Enhanced monitoring of biopharmaceutical product purity using liquid chromatography-mass spectrometry", Journal of Chromatography A, Jul. 2011, pp. 4340-4348, vol. 1218, No. 28.

Notification of Transmittal of the International Preliminary Report on Patentability dated Jun. 25, 2014 issued in related Application No. PCT/EP2013/058619.

* cited by examiner

QUANTIFICATION OF IMPURITIES FOR RELEASE TESTING OF PEPTIDE PRODUCTS

CROSS-REFERENCE TO RELATED APPLICATIONS

This application claims the benefit of International Patent Application No. PCT/EP2012/057771 filed on Apr. 27, 2012 and U.S. Provisional Application No. 61/665,098 filed on Jun. 27, 2012, the entire contents of each of which are incorporated herein by reference.

DESCRIPTION

The present invention relates to a method for the quantitative determination of an impurity present in a peptide product, wherein the impurity cannot be separated from the main product and optionally from other impurities. The method particularly involves the use of high resolution mass spectrometry (MS) detection with or without high performance liquid chromatography (HPLC). The method can be used for the investigation of the quality of peptides and proteins, particularly of pharmaceutical peptides and proteins, and formulations thereof.

Using well-known recombinant DNA and chemical solid phase synthesis processes, several proteins and peptides have been synthesized for pharmaceutical use. The production of these proteins and peptides, however, often leads to a multiplicity of undesired synthesis by-products. This is especially the case when they are produced by solid phase synthesis. With an increase in length of the peptide/protein, leading to an increase in the synthesis steps, these by-products may be present in 50 to 70% of the crude product.

Thus, an important part of the synthesis is the purification of the main product from the synthesis by-products. This purification is mainly done by chromatographic procedures. For use as an active ingredient in a pharmaceutical product, the final purified peptide product needs to be analyzed with regard to the purity, which is also done mostly using chromatographically procedures. Since the differences in the molecular structure of the desired peptide product and the undesired synthesis by-products are often very minor compared with the overall structure, the chromatographic properties of these products may be identical or nearly identical. This often leads to a co-elution of these impurities with other impurities and the main product itself in a chromatographic separation procedure.

The development of selective analytical methods is one of the key aspects for the release testing of peptide product compositions used as pharmaceutical compounds. But due to the reasons described above, even great efforts may not result in the separation of all relevant impurities by chromatographic methods. Thus, there is a need to provide novel methods for determining the amounts of impurities in peptide products, particularly the amount of impurities which cannot be quantitatively separated from the desired main product by chromatographic methods.

The present invention provides a method for the quantitative determination of impurities in peptide product compositions, which can not be separated chromatographically from the main product or which co-elute with other impurities or ingredients of the composition. This method is shown exemplarily for the peptide Lixisenatide (AVE0010), a GLP-1 agonist having a length of 44 amino acids long. The amino acid sequence of Lixisenatide is shown in SEQ ID NO:1:

H-G-E-G-T-F-T-S-D-L-S-K-Q-M-E-E-E-A-V-R-L-F-I-E-W-L-K-N-G-G-P-S-S-G-A-P-P-S-K-K-K-K-K-K-NH$_2$

Lixisenatide is produced by a chemical solid phase synthesis process. By means of chromatographic purification procedures, most of the impurities can be separated from the desired main product.

But nevertheless two impurities, Di-Ser(33)-AVE0010 and Di-Ala(35)-AVE0010, cannot be separated by chromatographic methods. The amino acid sequences of these impurities are as follows:

Di-Ser(33)-AVE0010
(SEQ ID NO: 2)
H-G-E-G-T-F-T-S-D-L-S-K-Q-M-E-E-E-A-V-R-L-F-I-E-W-L-K-N-G-G-P-S-S-S-G-A-P-P-S-K-K-K-K-K-K-NH$_2$

Di-Ala(35)-AVE0010
(SEQ ID NO: 3)
H-G-E-G-T-F-T-S-D-L-S-K-Q-M-E-E-E-A-V-R-L-F-I-E-W-L-K-N-G-G-P-S-S-G-A-A-P-P-S-K-K-K-K-K-K-NH$_2$

Since Lixisenatide is used as a pharmaceutical product, particularly in the treatment of diabetes patients, the presence and the amount of the above impurities has to be determined in order to allow batch release. The present inventors have now found that a quantitative determination of the above impurities may be achieved using high resolution mass spectrometric techniques with or without prior chromatography.

A subject matter of the present invention is a method for the quantitative determination of an impurity present in a peptide product composition, comprising the steps:
(a) providing a peptide product composition comprising a peptide product and an unknown amount of at least one impurity, wherein said impurity cannot be separated from the peptide product or another ingredient of the composition by a chromatographic procedure,
(b) providing at least one sample of the peptide product composition without said impurity added and optionally at least one further sample of the composition with a known amount of said impurity added,
(c) quantitatively determining said impurity in said at least one sample from step (b) by mass spectrometry, and
(d) calculating the amount of said impurity in the peptide product composition based on the results of (c).

A further subject matter of the present invention is a method for the quantitative determination of an impurity present in a peptide product composition, comprising the steps:
(a) providing a peptide product composition comprising a peptide product and an unknown amount of at least one impurity, wherein said impurity cannot be separated from the peptide product or another ingredient of the composition by a chromatographic procedure,
(b) providing at least three samples of the peptide product composition, wherein a first sample comprises the peptide product composition without said impurity added, and wherein at least two further samples comprise the peptide product composition each with a different known amount of said impurity added,
(c) quantitatively determining said impurity in said at least three samples from step (b) by mass spectrometry and
(d) calculating the amount of said impurity in the peptide product composition based on the results of (c).

A further subject matter of the invention is a reagent kit for determining the amount of impurities in a Lixisenatide (AVE 0010) product composition, comprising:

(i) at least one stock preparation of Di-Ser(33)-AVE0010 and/or (ii) at least one stock preparation of Di-Ala(35)-AVE0010.

Still, a further subject-matter of the invention is a method for the quality control of a composition comprising an exendin peptide product comprising the amino acid sequence S-S-G-A, preferably of a composition comprising a Lixisenatide (AVE0010) product, comprising quantitatively determining the amount of a Di-Ser(33)-peptide, e.g. Di-Ser(33)-AVE0010 and/or a Di-Ala(35)-peptide, e.g. Di-Ala(35)-AVE0010, in said composition.

The present invention relates to the determination of an impurity present in a peptide product composition. The term "peptide product" encompasses peptides and proteins having a length of at least 5 or at least 10 amino acids and up to 50 or up to 100 amino acids or even longer. The peptide product may consist of genetically encoded amino acid building blocks or may comprise non-genetically encoded amino acid building blocks, e.g. non-naturally occurring amino acids, D-amino acids or chemically modified amino acids or may consist of several peptide chains linked e.g. by disulfide bridges. The peptide product may further contain modifications at the N- and/or C-terminus and/or at side chains, e.g. an acylation, an amidation or the addition of non-peptide side chain groups such as lipophilic groups. The peptide product may be linear or circular. Preferably, the peptide product has a length from 5-100 amino acids.

The synthesis of the peptide product may involve recombinant DNA processes and/or chemical synthesis processes. Preferably, the peptide product has been chemically synthesized, particularly by a solid phase synthesis procedure which is well-known in the art, e.g. a procedure involving a stepwise elongation of a peptide chain coupled to a carrier, e.g. a synthetic resin. In a preferred embodiment of the invention, the peptide product is an Exendin peptide, e.g. Exendin-4, Liraglutide or Lixisenatide (AVE0010). Further examples of peptide products are insulins and insulin analogues or DPP-4 inhibitors. More preferably, the peptide product is an Exendin peptide, e.g. an Exendin peptide comprising the amino acid sequence S-S-G-A, most preferably Lixisenatide (AVE0010).

The method of the present invention involves the quantitative determination of an impurity present in a peptide product after its synthesis, e.g. after its synthesis by a solid phase synthesis procedure or as a degradation product after storage. The impurity is usually a peptide impurity, e.g. a peptide which differs from the desired main peptide product in at least one amino acid building block and/or a chemical modification. For example, the impurity may be a peptide which differs from the desired peptide product by at least one dimeric amino acid building block, i.e. a Di-serine or Di-alanine building block. In the case of an Exendin peptide, e.g. an Exendin peptide comprising the amino acid sequence S-S-G-A, the impurity may be e.g. a Di-Ser(33)-exendin peptide, a Di-Ala(35)-exendin peptide or combinations thereof. In the case of Lixisenatide, the impurity may e.g. be Di-Ser(33)-AVE0010, Di-Ala(35)-AVE0010 or combinations thereof.

The method of the present invention comprises the quantitative determination of at least one impurity in a peptide product composition. The peptide product composition comprises at least one peptide product and at least one impurity to be determined. Further, the composition may comprise other ingredients, e.g. peptide or non-peptide ingredients including other impurities. The peptide product composition may e.g. be a pharmaceutical formulation or a composition intended for the manufacture of a pharmaceutical formulation, e.g. a synthesized batch of the peptide product.

In the method of the present invention, the peptide product comprises an unknown amount of at least one impurity, which cannot be quantitatively separated from the peptide product by a chromatographic procedure or which co-elutes with other impurities or ingredients present in the peptide product sample. In some cases, the peptide product composition comprises unknown amounts of one impurity. In other cases, the peptide product composition comprises unknown amounts of at least two, e.g. 2, 3, 4, 5 or even more impurities which cannot be quantitatively separated from the peptide product by a chromatographic procedure or which co-elute with other other impurities or ingredients present in the peptide product sample. Preferably, the at least one impurity cannot be quantitatively separated from the peptide product.

The term "chromatographic procedure" involves a chromatographic procedure suitably for the purification of peptide products, including e.g. ion exchange chromatography, hydrophobic interaction chromatography, affinity chromatography, size exclusion chromatography, and particularly high performance liquid chromatography (HPLC) and more particularly Reverse Phase HPLC, or combinations of several procedures.

The impurity which is determined by the method of the present invention cannot be quantitatively separated from the peptide product or from other ingredients of the composition. This means, the impurity co-elutes or substantially co-elutes with the desired peptide product or with other impurities or ingredients after a chromatographic separation procedure, particularly after a chromatographic separation procedure as described above in such a way that quantification by optical methods, e.g UV- or fluorescence detection is not possible. This means, that the impurity cannot be separated from the desired peptide product or from other ingredients including impurities by reasonable efforts and its quantitative amount in a given batch of the peptide product composition has to be quantitatively determined by the method of the present invention.

Step (a) of the inventive method comprises providing a peptide product composition comprising an unknown amount of at least one impurity wherein that impurity cannot be separated from the peptide product or another ingredient of the composition by a chromatographic procedure as described above. The peptide product may e.g. be a product for use in pharmaceutical applications, e.g. for use as a medicament in human or veterinary medicine.

Step (b) of the inventive method involves providing at least one sample of the peptide product composition without added impurity and optionally at least one further sample of the peptide product composition with a known amount of added impurity. In a preferred embodiment, step (b) involves providing at least three samples of the peptide product composition wherein the first sample comprises the peptide product composition without added impurity in wherein at least two further samples comprise the peptide product composition and each of these samples additionally comprises a different known amount of added impurity.

At least one sample is a sample which comprises the peptide product composition without added impurity, i.e. an unspiked sample comprising an unknown amount of the impurity to be determined. In addition to this sample, at least one, e.g. at least two, three or four further samples may be provided which are spiked samples comprising the peptide product composition with the unknown amount of impurity and additionally with different known amounts of added impurity to be determined. These spiked samples may be prepared by adding the impurity to the un-spiked peptide product composition samples from a stock preparation of the impurity, preferably from at least two stock preparations comprising different concentrations of the impurity. The stock preparations may be present in any suitable form, e.g. preparations in dry or liquid form. Preferably the stock preparations are stock solutions.

The tested samples comprise the peptide product with an unknown amount of the impurity to be determined and optionally the added impurity. These compounds are present in concentrations, which allow analysis by mass spectrometry. The concentration of the peptide product may vary to a great extent. It may be e.g. in the range of 0.001-50 mg/ml, preferably 0.01-10 mg/ml and more, preferably 0.02-5.0 mg/ml, for example about 1.0 mg/ml. In the spiked samples, the amount of added impurity is preferably in the range of 0.1%-5%, preferably from 0.1-2% based on the concentration of the peptide product in the sample.

In a preferred embodiment, the method of the invention comprises the testing of an un-spiked peptide product sample together with at least one, preferably at least two, three or four or even more peptide product samples spiked with at least one impurity. In a different embodiment, the method of the invention involves the testing of only an un-spiked peptide product sample. The unknown amount of impurity present in the un-spiked sample may be determined by reference measurements of spiked samples and/or by comparing the measured value of the impurity in the un-spiked sample with a reference, e.g. a standard or calibration curve.

Step (c) of the inventive method comprises quantitatively determining said impurity in said at least one sample from step (b) by high resolution mass spectrometry. In addition to mass spectrometry, the determination may involve a prior chromatographic procedure, e.g. in order to separate other impurities from the peptide product or from other ingredients of the composition. Preferably, mass spectrometry is combined with HPLC. Each sample may subjected to several individual determinations in order to increase the accuracy of the measurement.

Mass spectrometry is based on a measurement of the mass-to-charge ratio of charged particles. In a typical mass spectrometry procedure, the sample is loaded onto the mass spectrometry instrument and volatilized. The sample components are ionized and the resulting ions are separated in the mass analyzer by electromagnetic fields. The resulting ions are detected and the signal is processed into a mass spectrum. For the ionization of peptide products, electrospray ionization (ESI) and matrix-assisted laser desorption/ionization (MALDI) may be used. The resulting ions may be detected by highly sensitive methods such as Orbitrap or Fourier Transform (FT)-Ion Cyclotron Resonance (ICR) detection systems.

According to step (c), at least one peak associated with the impurity to be determined is analyzed by mass spectrometry. This peak may be derived either from a deconvoluted or non-deconvoluted mass spectrum. Preferably, the method involves the determination of one or several monoisotopic peaks associated with the impurity to be determined. In the case of the impurity Di-Ser(33)-AVE0010, a quadruply charged peak of a non-deconvoluted mass spectrum at e.g. 1237.1529 Da or of the deconvoluted mass spectrum at 4944.5822 Da may be used. In case of the impurity Di-Ala(35)-AVE0010, a quadruply charged peak of the non-deconvoluted mass spectrum at 1233.1550 Da or of the deconvoluted mass spectrum at 4928.5908 Da may be analyzed.

The at least one peak to be analyzed may be identified in a mass spectrum of the impurity using a high resolution setting and a highly sensitive detection as described above.

Step (d) comprises calculating the amount of the impurity in the peptide product composition based on the mass spectrometry analysis results. In a preferred embodiment, the calculation is carried out by a method comprising a regression analysis, particularly a linear regression analysis. The regression analysis may comprise generating a curve, e.g. a straight line, from the measured values of the impurity in at least two spiked samples, i.e. samples comprising the peptide product with the unknown amount of impurity and having added the two different known amounts of impurities (or from reference values of such samples which have been generated in standard or calibration measurements). Into this curve, e.g. a straight line, the measured value of the impurity in the un-spiked sample is inserted thereby allowing quantitative determination of the unknown amount of the impurity present in that sample.

Preferably, the calculation is carried out according to the linear straight line equation:

$$y=ax+b$$

wherein y corresponds to the determined peak area of the impurity in a sample (either spiked or un-spiked sample), x corresponds to the known added amount of the impurity in a spiked sample, a is the straight line slope and b is the intercept with the y-axis, which corresponds to the measurement signal of the impurity in a sample without added impurity (x=0). The quantitative amount of impurity in the un-spiked sample $x_t$ may be obtained using the obtained regression parameters as follows:

$$x_t=b \cdot a^{-1}$$

The invention also encompasses a reagent kit for determining the amount of impurities in a Lixisenatide product which comprises at least one stock preparation of Di-Ser(33)-AVE0010 and/or Di-Ala(35)-AVE0010 and optionally further reagents such as solvents, buffers etc. The reagent kit may be used in a method for the quality control of a Lixisenatide product for the quantitative determination of the amount of Di-Ser(33)-AVE0010 and/or Di-Ala(35)-AVE0010 in said Lixisenatide product. Preferably, the quantitative determination is carried according to a mass spectrometric method, e.g. a mass spectrometric method as described above.

The present invention is explained in more detail by the following Figures and Examples.

LEGENDS OF FIGURES

(FIG. 7A) and Di-Ser(33)-AV0010 (FIG. 7B) in a test sample as a non-deconvoluted mass spectrum.

Figure 8A:
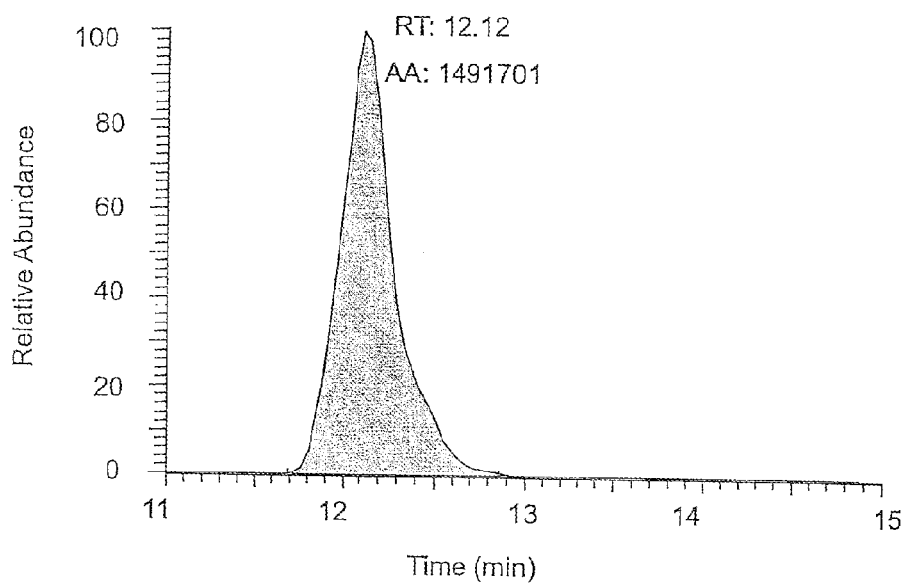
Figure 8A:
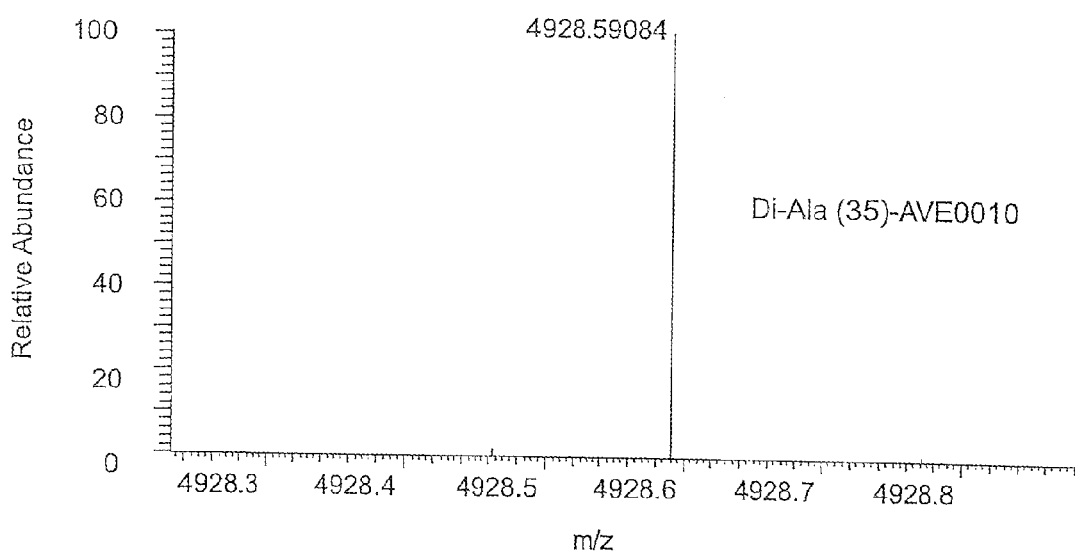
Figure 8B:
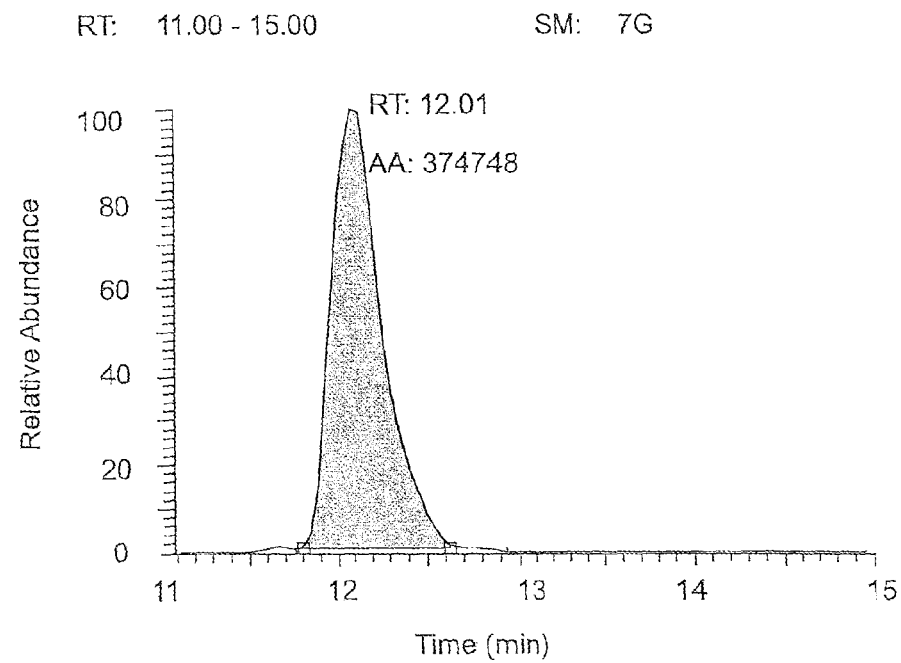
Figure 8B:
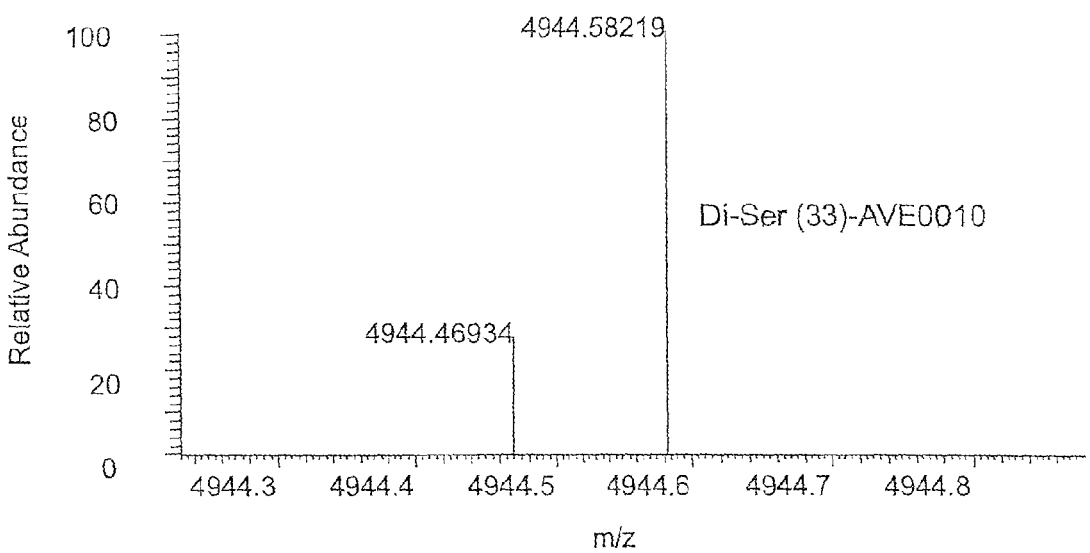

FIGS. 8A and 8B show an extracted single ion chromatogram of Di-Ala(35)-AVE0010 (FIG. 8A) and Di-Ser(33)-AV0010 (FIG. 8B) in a test sample as a deconvoluted mass spectrum.

Figure 9:
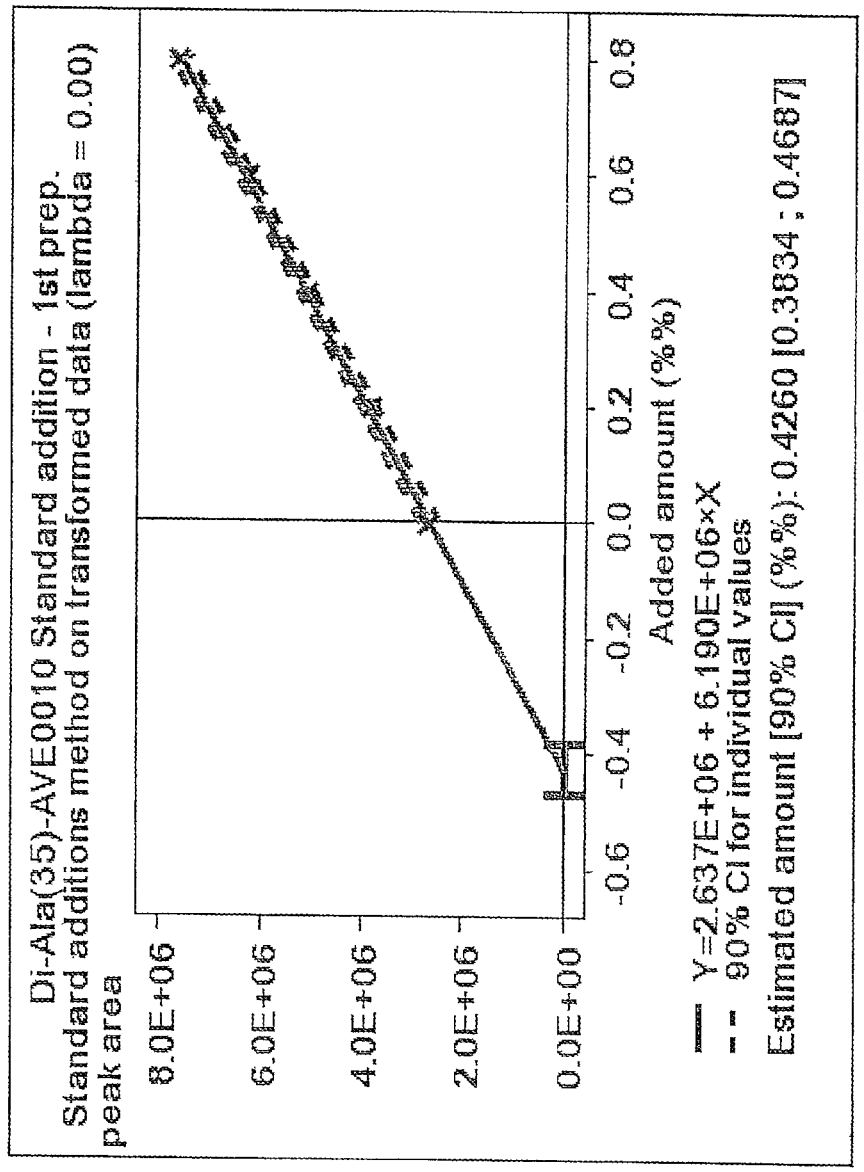

FIG. 9 shows an example for calculation of the concentration of the impurity Di-Ala(35)-AVE0010 in a test sample.

EXAMPLES

Analytical Procedure for Quantification of Di-Ser(33)-Lixisenatide and Di-Ala(35)-Lixisenatide by HPLC/MS 1. Materials and Methods
1.1 Reference Materials Lixisenatide (AVE0010) Reference material; produced by solid phase synthesis, followed by purification.

Di-Ser(33)-AVE0010 Reference material; produced by solid phase synthesis process with double coupling steps of the protected amino acid Serine at position 33, followed by purification.

Di-Ala(35)-AVE0010 Reference material; produced by solid phase synthesis process with double coupling steps of the protected amino acid Alanine at position 35, followed by purification.

An un-spiked sample preparation of Lixisenatide (containing unknown amounts of impurities DiSer(33)-AVE0010 and DiAla(35)-AVE0010) was prepared at a concentration of 1.0 mg Lixisenatide/ml.

Four spiked sample preparations for each of the impurities were prepared by incorporating 0.2%, 0.4%, 0.6% and 0.8% by weight of the impurities Di-Ser(33)-AVE0010 or Di-Ala(35)-AVE0010, respectively, in a sample preparation with 1.0 mg Lixisenatide/ml.

1.2 Analytical Conditions

A gradient high performance liquid chromatographic system consisting of a binary HPLC pump, an autosampler, column oven, and a high resolution mass spectrometer e.g. LTQ-Orbitrap (ThermoFisher) with a resolution setting of 100.000 (at m/z 400), or equivalent was used.

Chromatography was performed with a C18 Reversed Phase analytical HPLC column (Jupiter C18 3 μm 300A) with a length of 150 mm and an internal diameter of 2.0 mm.

Mobile Phase A consisted of 850 volume parts water, 150 volume parts acetonitrile and 1 volume part trifluoroacetic acid. Mobile Phase B consisted of 250 volume parts water, 750 volume parts acetonitrile and one volume part trifluoroacetic acid. The gradient was set as follows:

| Time [minutes] | Mobile phase A [%] | Mobile Phase B [%] |
|---|---|---|
| 0.00 | 77.5 | 22.5 |
| 17.50 | 28.0 | 72.0 |
| 17.51 | 77.5 | 22.5 |
| 26.00 | 77.5 | 22.5 |

The mass spectrometer was operated in positive electrospray ionization mode and scanned in a way to measure the ion signals from the analytes to determined.

The test conditions were as follows:

| | | |
|---|---|---|
| Flow rate: | 0.25 mL/min | |
| Injection volume: | 10 μL | |
| Autosampler temperature: | Set autosampler temperature at +10° C. ± 2° C. | |
| Column temperature: | Set oven temperature at +25° C. ± 2° C. | |
| Ionization method: | ESI positive | |
| Measurement/ Detection: | ITMS: | mode: positive mass range: 700.0-2000.0 |
| | FTMS: | mode: positive mass range (SIM) 1232.0-1239.0 resolution: 100,000 |
| | Divert Valve: | waste 0-1.5 min inject 1.5 2.25.5 min |
| | PDA total scan (UV), optional | |

The procedure was based on the methods described in Ph. Eur 7.0 (2011) (2.2.43 Mass Spectrometry) and USP 34 (2011) (<736> Mass Spectrometry).

1.3 Integration

Determinations were performed either from the deconvoluted mass spectra or the non-deconvoluted mass spectra of the quadruply charged ions $[M+4H^+]^{4+}$.

After selection of the accurate mass of a single isotopic peak of the pattern:
a) using a quadruply charged peak of the non deconvoluted mass spectra:

| | |
|---|---|
| DiSer(33)-AVE0010: | e.g. 1237.1529 Da |
| DiAla(35)-AVE0010: | e.g. 1233.1550 Da, | or b) using the deconvoluted mass spectra:

| | |
|---|---|
| DiSer(33)-AVE0010: | e.g. 4944.5822 Da |
| DiAla(35)-AVE0010: | e.g. 4928.5908 Da, | extracted ion chromatograms were performed. Only the isotope of interest was extracted. The peaks from the extracted ion chromatograms were integrated.

2. Results

Figure 1:
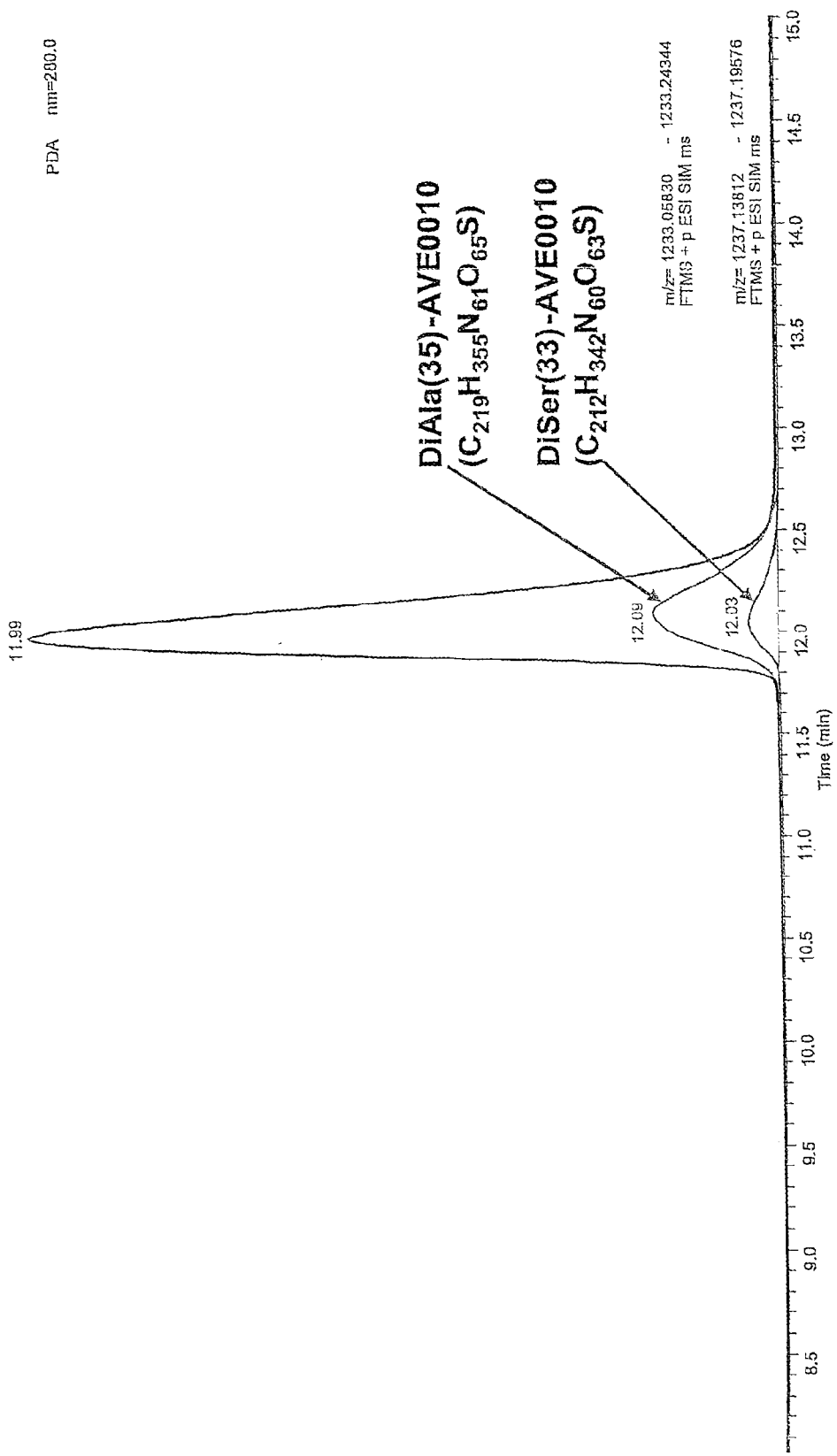
FIG. 1 shows the co-elution of the peaks of Lixisenatide (AVE0010), Di-Ser(33)-AVE0010 and Di-Ala(35)-AVE0010 in an HPLC chromatogram.

FIG. 1 shows the co-elution of the peaks for Lixisenatide and the impurities Di-Ala(35)-AVE0010 and Di-Ser(33)-AVE0010 in an HPLC chromatogram. Due to these overlaps in the chromatographic peaks, Di-Ala(35)-AVE0010 and Di-Ser(33)-AVE0010 constitute impurities which cannot be quantitatively separated from the desired peptide product AVE0010 by a chromatographic procedure.

Figure 2:
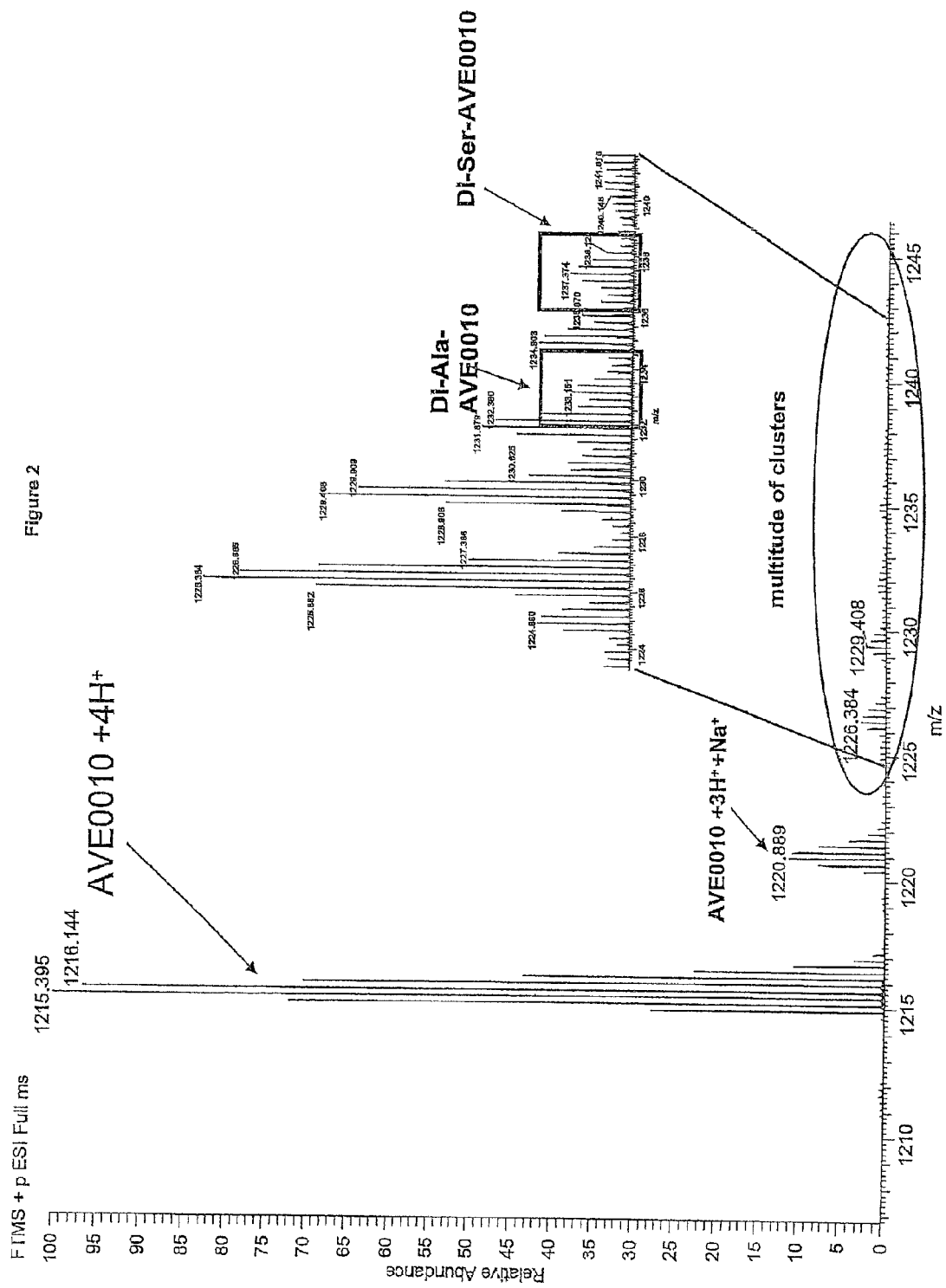
FIG. 2 shows the mass spectrum of the quadruply charged molecular ions of AVE0010 and the impurities Di-Ser(33)-AVE0010 and Di-Ala(35)-AVE0010.

For the method development some specific features of mass spectrometry had to be taken into account. The mass spectrum of Lixisenatide shows besides the multiply protonated species typically clustering with cations that are ubiquitous in solution, e.g. sodium or potassium. FIG. 2 shows the spectrum section of the quadruply charged ions of AVE0010 which overlap with the mass spectra of the impurities and thereby obscure the analyte.

Figure 3:
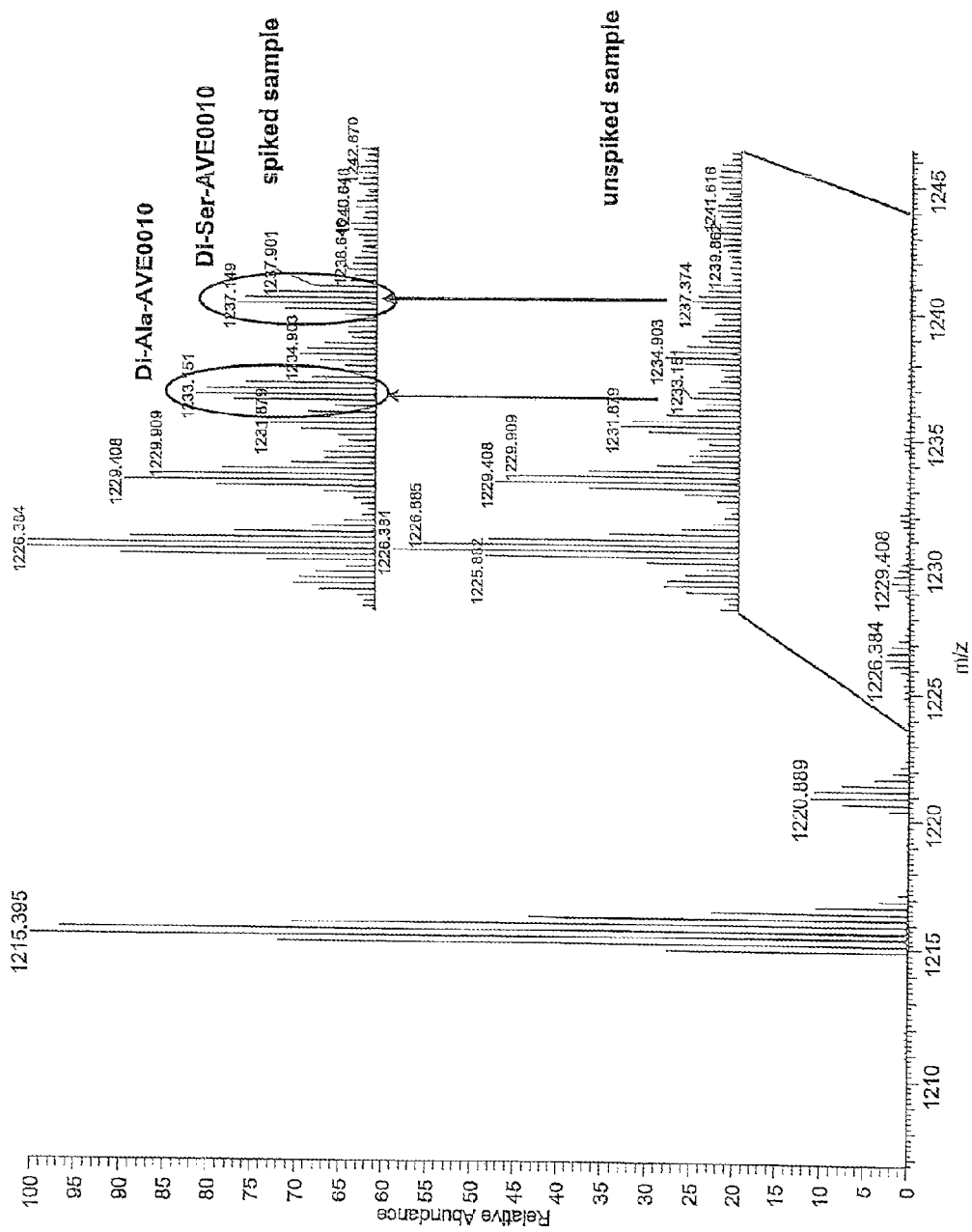
FIG. 3 shows a comparison of mass spectra of un-spiked and spiked (1% of each impurity) AVE0010 preparations.

In FIG. 3 an AVE0010 sample spiked with 1% of the two impurities is compared with an un-spiked sample containing yet a low amount of the impurities. In the expanded view of the inset can be seen, that there may be an overlap of the molecular patterns with underlying clusters. In the case of Di-Ser(33)-AVE0010 the mass increase relative to Lixisenatide is 87 Da. On the other hand, Lixisenatide can cluster with 4 sodium ions leading to a mass shift of 88 Da. These two patterns overlap and have to be separated mass-spectrometrically otherwise the Di-Ser-AV0010 impurity cannot be quantified specifically.

Figure 4:
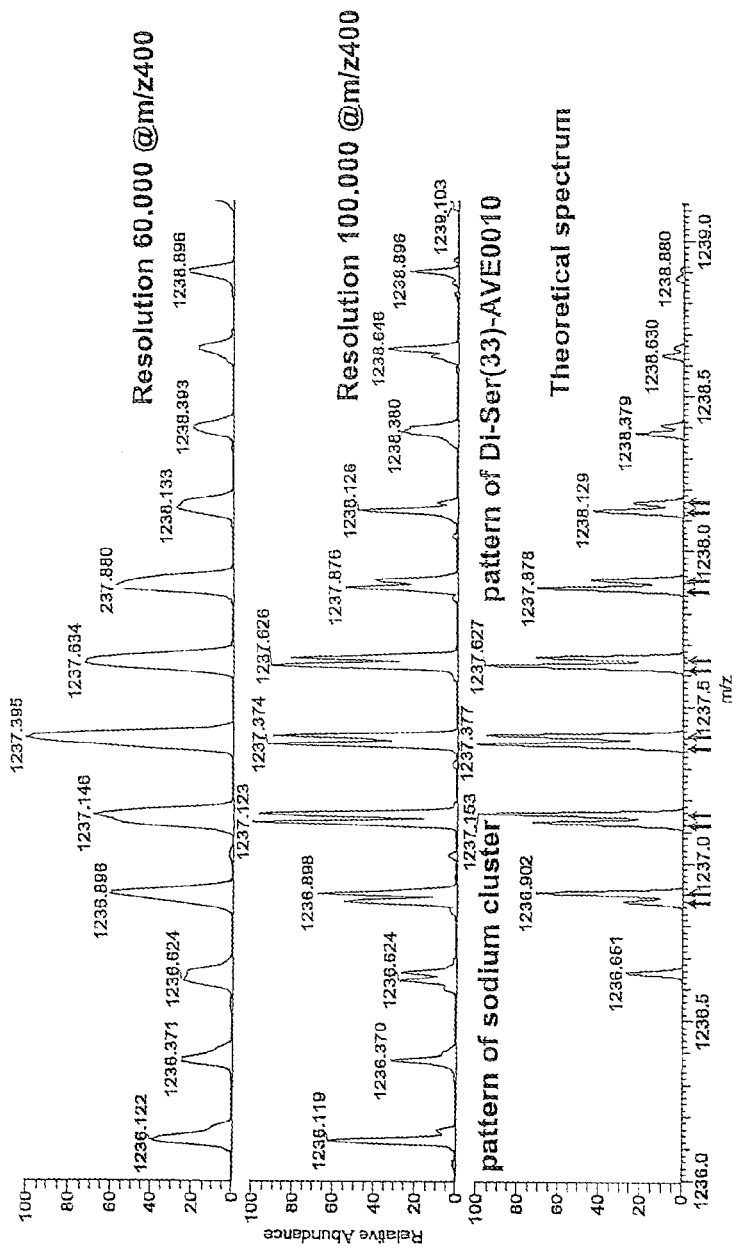
FIG. 4 shows an expanded view of the mass range of Di-Ser(33)-AVE0010 at the resolution setting of 60,000 and 100,000 respectively at m/z 400 and the theoretical calculated pattern of overlapping species.

As can be seen in FIG. 4, the overlapping peaks were not separated with a resolution setting of 60.000 but only with a resolution setting of 100.000. In the lower part of FIG. 4 the theoretical spectrum of Di-Ser-AVE0010 overlapping with the sodium cluster of Lixisenatide is shown. Such high resolutions are preferably delivered by Fourier transform mass spectrometry, either FT-ICR or as used here by an FT-Orbitrap mass spectrometer.

Figure 5:
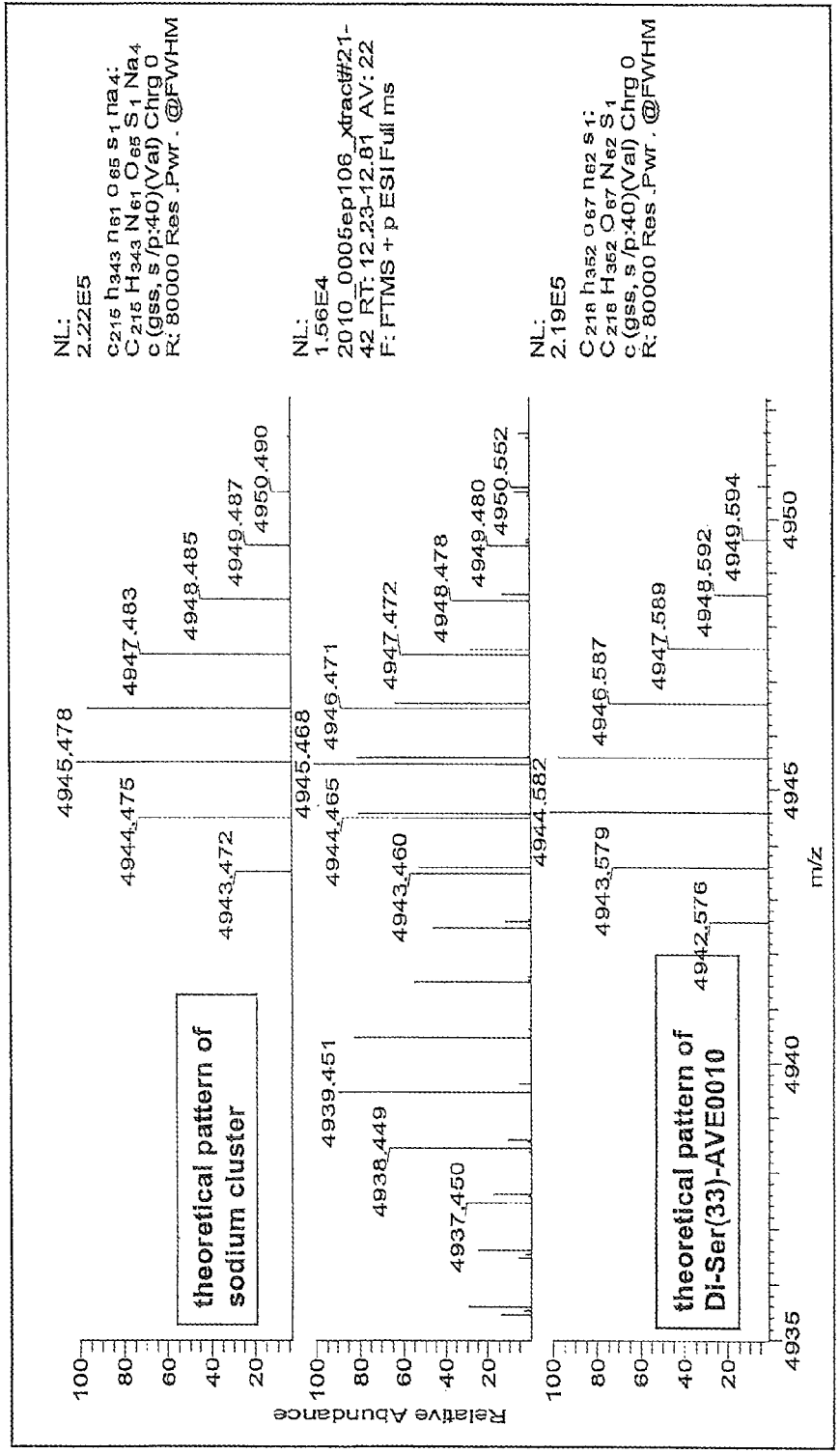
FIG. 5 shows deconvoluted mass spectra with theoretical calculated patterns of overlapping species.

After deconvolution and centroiding of the spectra, these two species may be separated mass-spectroscopically, c.f. FIG. 5.

Figure 6:
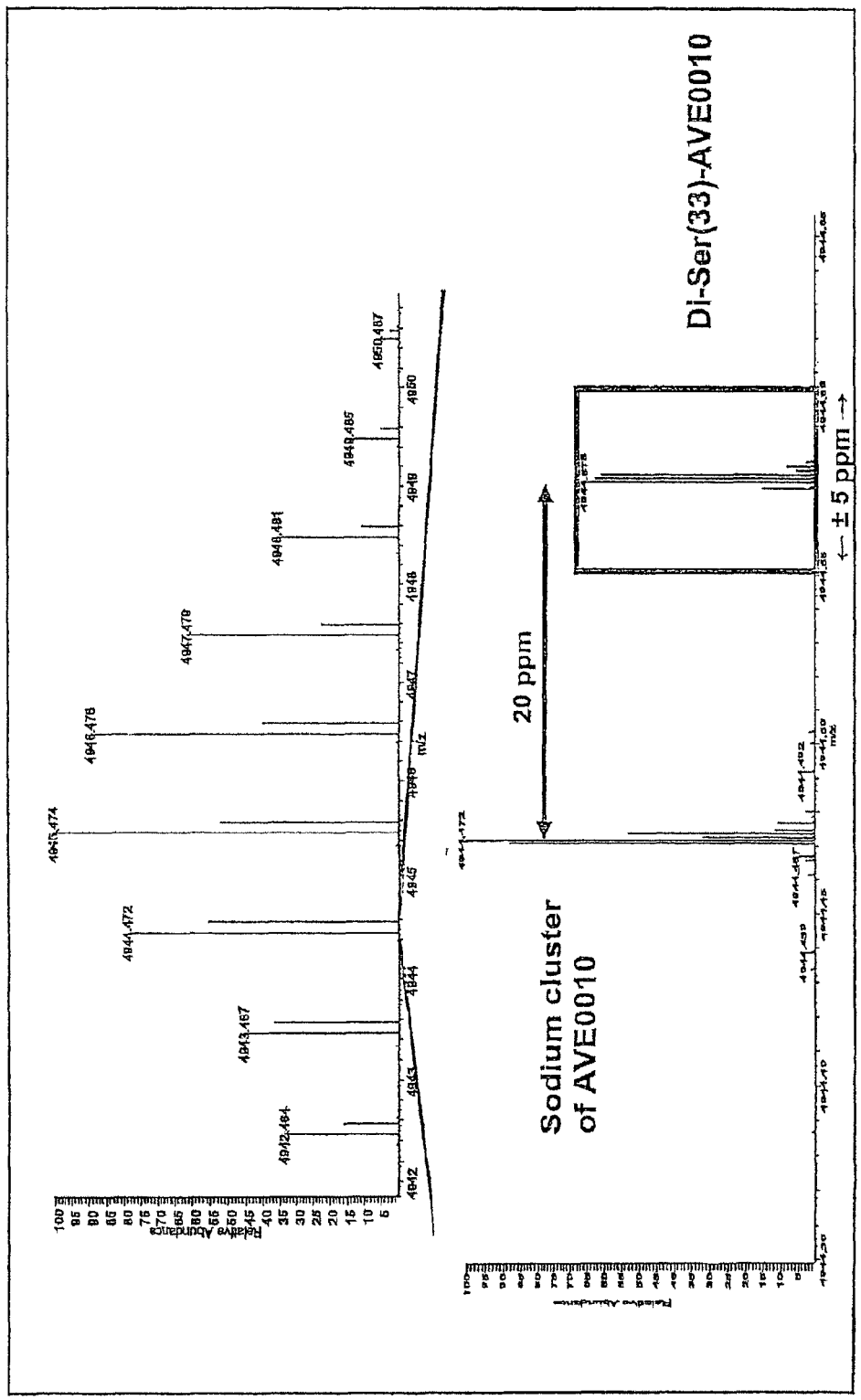
FIG. 6 shows an expanded view on the impurity peak used for the quantification of Di-Ser(33)-AVE0010.

In FIG. 6 all measured individual mass spectra of the complete chromatographic peak have been added. The mass peak used for the measurement of Di-Ser(33)-AVE0010 is shown in an expanded view. It is sufficiently distant from the peak corresponding to the sodium cluster of AVE0010 to allow an accurate measurement. All analyte mass peaks fall within a narrow mass window, showing the mass stability of the instrument, well separated from any interfering peak. Therefore this method is suited to determine specifically the amounts of Di-Ser(33)-AVE0010 and Di-Ala(35)-AVE0010 in a Lixisenatide peptide product.

Figure 7A:
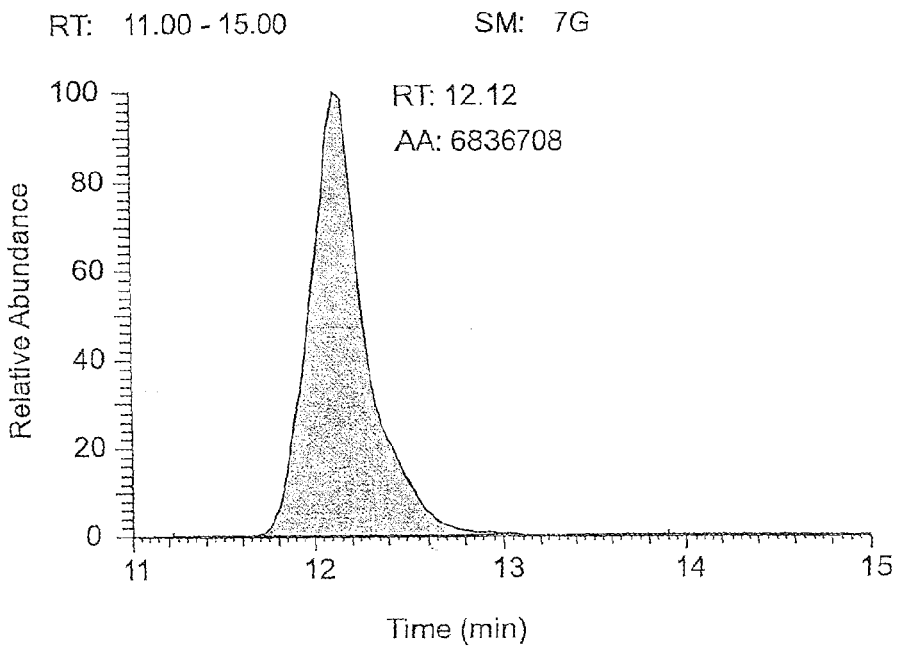
FIGS. 7A and 7B show an extracted single ion chromatogram of a quadruply charged isotope of Di-Ala(35)-AVE0010
Figure 7A:
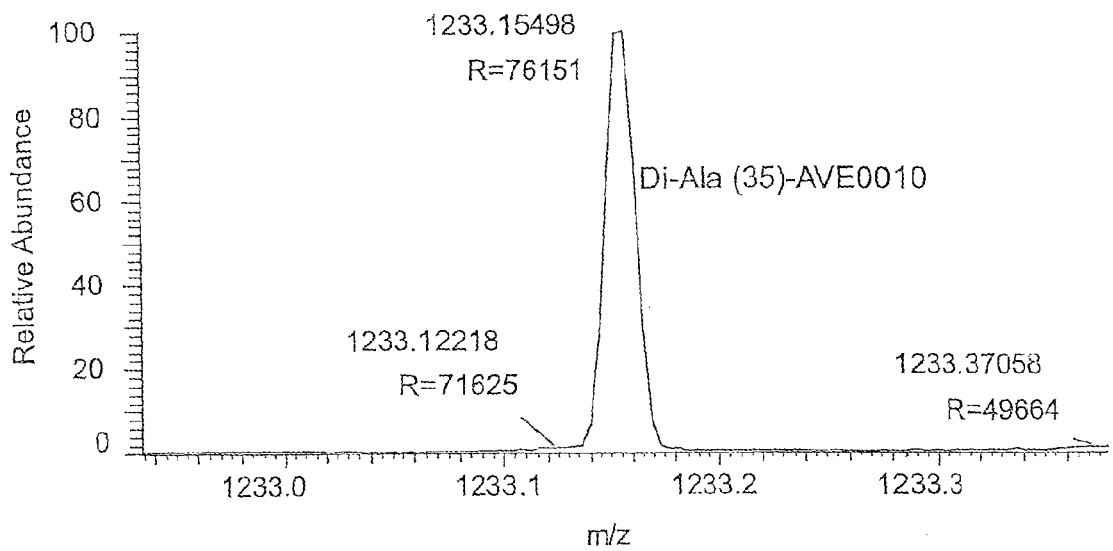
Figure 7B:
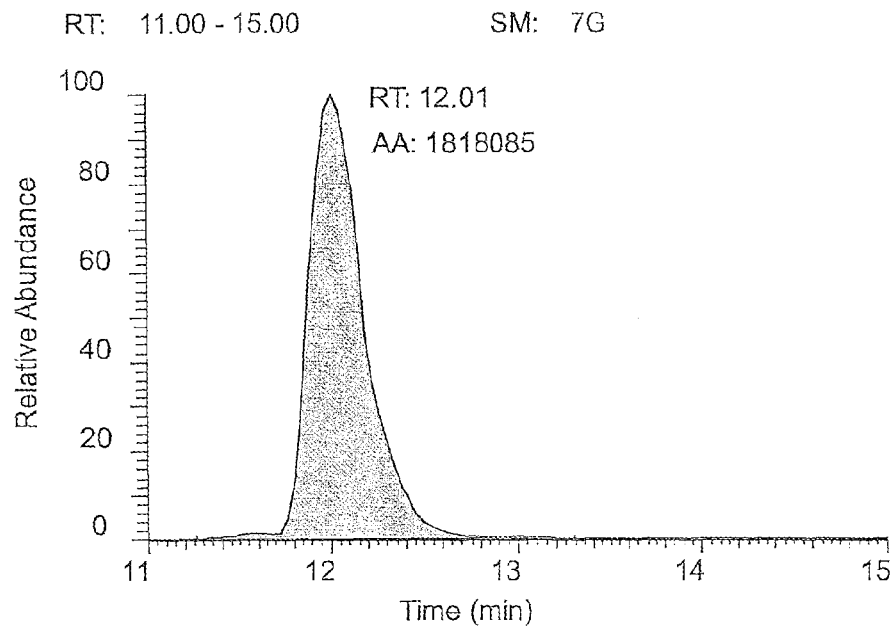
Figure 7B:
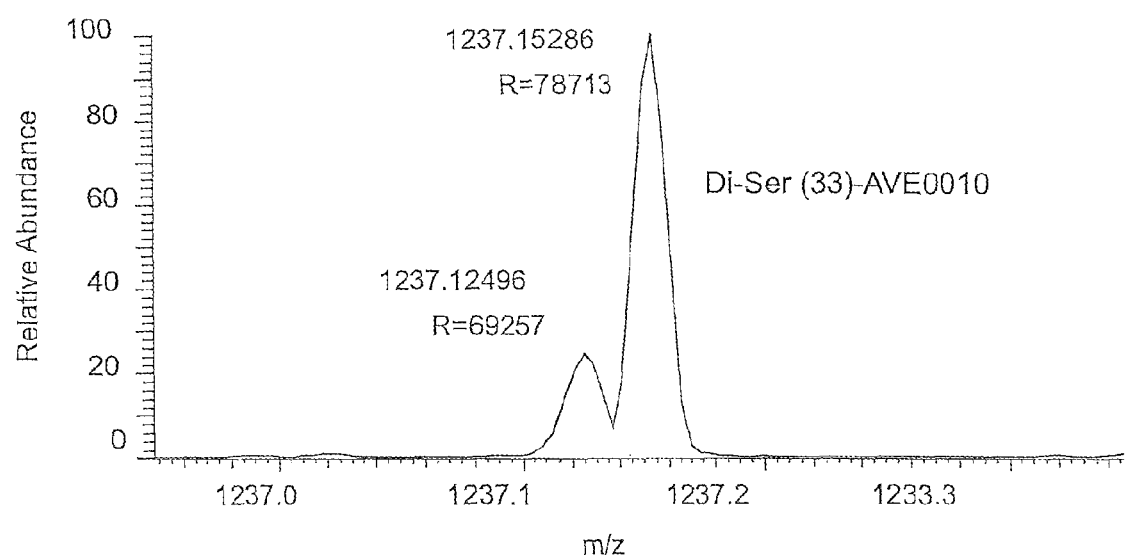

The extracted ion chromatograms of a quadruply charged isotope of Di Ala(35)-AVE0010 and Di-Ser(33)-AV0010 in a test sample are shown as non-deconvoluted mass spectra in FIGS. 7A and 7B and as deconvoluted mass spectra in FIGS. 8A and 8B.

The amount of Di-Ser(33)-AVE0010 and Di-Ala(35)-AVE0010 may be calculated by a linear regression analysis. By using each injection of the spiked and un-spiked test solutions, a regression curve may be established according to the equation:

$$y = ax + b$$

a = Slope
y = Peak area of test solutions (un-spiked and spiked test solutions)
x = Added amount of the Di-Ser(33)-AVE0010 or Di-Ala(35)-AVE0010 in test solutions (unspiked and spiked test solutions).
b = Intercept The concentration $x_t$ of Di-Ser(33)-AVE0010 and Di-Ala(35)-AVE0010 in the test sample may be calculated using the regression parameters obtained as follows:

$$x_t = b \cdot a^{-1}$$

FIG. 9 shows an example for calculation of the concentration Di-Ala(35)-AVE0010 in the test sample.

The final result was determined as the arithmetic mean of all individual determinations expressed in percent of Lixisenatide. In the specific case, the mean value of the impurity Di-Ala(35)-AVE0010 in the sample was determined as 0.4260% based on the amount of Lixisenatide.

---

The invention claimed is:

1. A reagent kit for determining the amount of impurities in a Lixisenatide (AVE 0010) product composition, comprising:
   (i) at least one stock preparation of Di-Ser(33)-AVE0010 (SEQ ID NO:2) H-G-E-G-T-F-T-S-DL-S-K-Q-M-E-E-E-A-V-R-L-F-I-E-W-L-K-N-G-G-P-S-S-S-G-A-P-P-S-K-K-K-K-K-K-NH₂ and/or
   (ii) at least one stock preparation of Di-Ala(35)-AVE0010 (SEQ ID NO:3) H-G-E-G-T-F-T-S-D-L-S-K-Q-M-E-E-E-A-V-R-L-F-I-E-W-L-K-N-G-G-P-S-S-G-A-A-P-P-SK-K-K-K-K-NH2.

2. A method for the quality control of a composition comprising an exendin peptide product comprising the amino acid sequence S-S-G-A, comprising quantitatively determining the amount of a Di-Ser(33)-peptide, and/or a Di-Ala(35)-peptide, in said composition.

3. The method of claim 2, wherein the quantitative determination is carried out according to a method comprising the steps:

(a) providing a composition comprising a peptide product and an unknown amount of at least one impurity, wherein said impurity cannot be separated from the peptide product or another ingredient of the composition by a chromatographic procedure and wherein said impurity co-elutes or substantially co-elutes with the desired peptide product after the chromatographic separation procedure,
   (b) providing at least one sample of said composition without said impurity added and at least one further sample of said composition with a known amount of said impurity added,
   (c) quantitatively determining said impurity in said sample from step (b) by mass spectrometry, and
   (d) calculating the amount of said impurity in said composition based on the results of (c).

4. The method of claim 2, wherein the composition comprises lixisenatide.

* * * * *

SEQUENCE LISTING

```
<160> NUMBER OF SEQ ID NOS: 3

<210> SEQ ID NO 1
<211> LENGTH: 44
<212> TYPE: PRT
<213> ORGANISM: Artificial Sequence
<220> FEATURE:
<221> NAME/KEY: SOURCE
<222> LOCATION: 1..44
<223> OTHER INFORMATION: /mol_type="protein"
      /note="Lixisenatide-(AVE0010)"
      /organism="Artificial Sequence"
<220> FEATURE:
<221> NAME/KEY: MOD_RES
<222> LOCATION: 44
<223> OTHER INFORMATION: Lysine is modified with an NH2 group.

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 45
<212> TYPE: PRT
<213> ORGANISM: Artificial Sequence
<220> FEATURE:
<221> NAME/KEY: SOURCE
<222> LOCATION: 1..45
<223> OTHER INFORMATION: /mol_type="protein"
      /note="Di-Ser(33)-AVE0010"
      /organism="Artificial Sequence"
<220> FEATURE:
<221> NAME/KEY: MOD_RES
<222> LOCATION: 45
<223> OTHER INFORMATION: Lysine is modified with an NH2 group.
```

```
<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Ser Gly Ala Pro Pro Ser Lys Lys Lys Lys Lys
        35                  40                  45

<210> SEQ ID NO 3
<211> LENGTH: 45
<212> TYPE: PRT
<213> ORGANISM: Artificial Sequence
<220> FEATURE:
<221> NAME/KEY: SOURCE
<222> LOCATION: 1..45
<223> OTHER INFORMATION: /mol_type="protein"
      /note="Di-Ala(35)-AVE0010"
      /organism="Artificial Sequence"
<220> FEATURE:
<221> NAME/KEY: MOD_RES
<222> LOCATION: 45
<223> OTHER INFORMATION: Lysine is modified with an NH2 group.

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Ala Pro Pro Ser Lys Lys Lys Lys Lys Lys
        35                  40                  45
```